(12) United States Patent
Ivona

(10) Patent No.: US 10,246,683 B2
(45) Date of Patent: Apr. 2, 2019

(54) METHOD AND ASSEMBLY FOR EXTRACTION OF REGENERATIVE CELLULAR COMPONENTS FROM ADIPOSE TISSUE

(71) Applicant: MyStem Limited, Nicosia (CY)

(72) Inventor: Piergiuseppe Ivona, Bari (IT)

(73) Assignee: MyStem Limited, Nicosia (CY)

( * ) Notice: Subject to any disclaimer, the term of this patent is extended or adjusted under 35 U.S.C. 154(b) by 19 days.

(21) Appl. No.: 15/329,792

(22) PCT Filed: Jul. 31, 2014

(86) PCT No.: PCT/EP2014/066465
§ 371 (c)(1),
(2) Date: Jan. 27, 2017

(87) PCT Pub. No.: WO2016/015767
PCT Pub. Date: Feb. 4, 2016

(65) Prior Publication Data
US 2017/0198259 A1 Jul. 13, 2017

(51) Int. Cl.
| C12N 5/0775 | (2010.01) |
| C12M 1/00 | (2006.01) |
| A61K 35/35 | (2015.01) |
| C12M 1/33 | (2006.01) |
| C12M 3/04 | (2006.01) |

(52) U.S. Cl.
CPC ............ *C12N 5/0667* (2013.01); *A61K 35/35* (2013.01); *C12M 27/10* (2013.01); *C12M 29/04* (2013.01); *C12M 45/02* (2013.01); *C12M 47/04* (2013.01)

(58) Field of Classification Search
CPC ..... C12N 5/0667; C12M 47/04; C12M 29/04; C12M 27/10; C12M 45/02; A61K 35/35
See application file for complete search history.

(56) References Cited

U.S. PATENT DOCUMENTS

2006/0051865 A1 3/2006 Higgins et al.
2013/0034524 A1* 2/2013 Agha-Mohammadi ......................
C12N 5/0667
424/93.7

FOREIGN PATENT DOCUMENTS

| EP | 2667024 A1 | 12/2013 |
| WO | 2012148350 A1 | 11/2012 |
| WO | 2013144883 A2 | 10/2013 |

OTHER PUBLICATIONS

Definition for Assembly. 2018. downloaded from www.definitions.net/definition/assernbly. p. 1-3 (Year: 2018).*
Doi Kentaro et al.,Enrichment isolation of adipose-derived stem/stromal cells from the liquid portion of liposuction aspirates with the use of an adherent column, Cytotherapy, Mar. 1, 2014, vol. 16 , Issue 3,381-391.
Ziqing Dong et al., In vivo injectable human adipose tissue regeneration by adipose-derived stem cells isolated rrom the fluid portion of liposuction aspirates,Tissue and Cell, Jun. 1, 2014, vol. 46, Issue 3, pp. 178-184, © 2014 Elsevier Ltd.
Michael P. Francis et al., Isolating adipose-derived mesenchymal stem cells from lipoaspirate blood and saline fraction, Organogenesis vol. 6 , Iss. 1, 2010.
Ahmad Ghorbani et al, Isolation of adipose tissue mesenchymal stem cells without tissue destruction: a non-enzymatic method, Tissue and Cell, vol. 46, Issue 1, Feb. 2014, pp. 54-58.
Carolina F. Markarian et al., Isolation of adipose-derived stem cells: a comparison among different methods, Biotechnology Letters, Apr. 2014, vol. 36, Issue 4, pp. 693-702.
Patricia A. Zuk et al, Human Adipose Tissue Is a Source of Multipotent Stem Cells, Mol. Biol. Cell Dec. 1, 2002 vol. 13, No. 12, 4279-4295.
Chen Da-Chung et al, Purification of human adipose-derived stem cells from fat tissues using PLGA/silk screen cybrid membranes, Biomaterials, vol. 35, Issue 14, May 2014, pp. 4278-4287.
Wu Cheng-Han et al., The isolation and differentiation of human adipose-derived stem cells using membrane filtration, Biomaterials, vol. 33, Issue 33, Nov. 2012, pp. 8228-8239.
Dora Reis Passinhas, Written Opinion of the International Searching Authority (ISA) for Application No. PCT/EP2014/066465, European Patent Office (EPO), dated Dec. 4, 2014.

* cited by examiner

*Primary Examiner* — Taeyoon Kim
(74) *Attorney, Agent, or Firm* — Florek & Endres PLLC

(57) ABSTRACT

The present invention concerns a novel method and assembly for extraction of regenerative cellular components from an adipose tissue, the method comprising the steps of filtering a harvested adipose tissue for recovering its liquid fraction by means of a filtering element having a first cut-off value comprised between 40 microns and 70 microns; separating regenerative cellular components present in the liquid fraction by means of cell size segregation which blocks cells bigger than a second cut-off value ranging from 8 to 20 microns; and recovering the regenerative cells-rich fraction comprising the regenerative cellular components not having being blocked during the separating step.

28 Claims, 2 Drawing Sheets

METHOD AND ASSEMBLY FOR EXTRACTION OF REGENERATIVE CELLULAR COMPONENTS FROM ADIPOSE TISSUE

TECHNICAL FIELD

The present invention concerns a novel method and assembly for extraction of regenerative cellular components from an adipose tissue.

Throughout the present description and in the appended claims the expression "regenerative cellular components of adipose tissue", refers to stromal vascular fraction and/or extracellular matrix of adipose tissue.

Stromal Vascular Fraction (SVF) and extracellular matrix (ECM) are products of lipoaspirate which are generally obtained from liposuction of excess adipose tissue. The lipoaspirate is a disposable byproduct of liposuction which contains a large population of stem cells called adipose derived stem cells (ADSCs).

Thus, the present invention particularly concerns the extraction of stromal vascular fraction and/or extracellular matrix from adipose tissue.

In particular, the assembly according to the present invention consists of a sterile closed system for extracting regenerative cellular components from the liquid and/or solid fraction of an adipose tissue and allowing concentrating of the regenerative cellular components in a very short time.

BACKGROUND OF THE INVENTION

Stem cells are a population possessing 1) self-renewal capacity, 2) long-term viability, and 3) multilineage potential.

The multilineage potential of embryonic stem cells and adult stem cells from the bone marrow has been characterized extensively. Although embryonic stem cell potential is enormous, many ethical and political issues accompany their use. Therefore, adult stem cells from the bone marrow stroma (i.e., mesenchymal stem cells, MSCs) have been proposed as an alternative source.

Originally identified as a source of osteoprogenitor cells, MSCs differentiate into adipocytes, chondrocytes, osteoblasts, and myoblasts in vitro (Hauner et al., 1987; Grigoradis et al., 1988; Wakitani et al., 1995; Ferrari et al., 1998; Johnstone et al., 1998; Pittenger et al., 1999) and undergo differentiation in vivo (Benayahu et al., 1989; Bruder et al., 1998a), making these stem cells promising candidates for mesodermal defect repair and disease management.

However, the clinical use of MSCs has presented problems, including pain, morbidity, and low cell number upon harvest. This has led many researchers to investigate alternate sources for MSCs.

Adipose tissue, like bone marrow, is derived from the mesenchyme and contains a supportive stroma that is easily isolated. Based on this, adipose tissue may represent a source of stem cells that could have far-reaching effects on several fields.

Applicant has identified a putative stem cell population within human lipoaspirates. This cell population, called processed lipoaspirate (PLA) cells, can be isolated from adipose tissue in significant numbers and exhibits stable growth and proliferation kinetics in culture. Moreover, PLA cells, like MSCs, differentiate in vitro toward the osteogenic, adipogenic, myogenic, and chondrogenic lineages when treated with established lineage-specific factors.

Based on the multilineage differentiation capacity of PLA cells, Applicant recognized that a population of multipotent stem cells, comparable with MSCs, can be isolated from human adipose tissue.

When collecting human adipose tissue, usually a compound of a liquid fraction and a dense fraction of the adipose tissue is gathered.

Up to now, regenerative cells of the adipose tissue are recovered starting from the collected dense fraction: the collected compound is first filtrated in order to separate the dense fraction from the liquid fraction, the latter being usually discarded.

Subsequently, the dense fraction is added with specific reagents (e.g. enzymes).

After a reaction time usually lasting around 30 to 60 minutes, the digested dense fraction of the adipose tissue is subjected to centrifugation which leads to the separation of the different phases (adipose portion and fluid portion) of the dense fraction and to the precipitation of a pellet rich of regenerative cells.

SUMMARY OF THE INVENTION

Applicant realized that, the use of reagents for the preparation of the dense fraction from which recovering the regenerative cells, leads to the deterioration of the extracellular matrix (ECM) of the regenerative cells.

Applicant also recognized that the recovery of regenerative cells with extracellular matrix is particularly desirable since the extracellular matrix confers structure to the regenerative cells, being a collagen which binds the regenerative cells.

Furthermore, Applicant realized that the liquid fraction of the adipose tissue which is usually discarded after having been separated from the dense fraction is also rich of regenerative cells. Thus, a recovery of the regenerative cells comprised in the liquid fraction of the adipose tissue is particularly desirable.

Thus, according to a first aspect of the present invention, a method for extracting regenerative cellular components from adipose tissue is provided comprising the steps of:
a) filtering a harvested adipose tissue for recovering its liquid fraction by means of a filtering element having a first cut-off value comprised between 40 microns and 70 microns;
b) separating regenerative cellular components present in the liquid fraction by means of cell size segregation which blocks cells bigger than a second cut-off value ranging from 8 to 20 microns; and
c) recovering the regenerative cells-rich fraction comprising the regenerative cellular components not having being blocked during the separating step b).

Advantageously, the method for extracting regenerative cellular components from adipose tissue according to the invention is capable of recovering regenerative cells from the liquid fraction of the adipose tissue.

In detail, Applicant identified that the regenerative cells which can be found in suspension in the liquid fraction of the collected adipose tissue have a very small size, usually around few microns.

In order to recover such small-sized cells, a filter having a correspondingly small mesh must be used. However, such small mesh filters tend to clog very easily depending on the density of the solution to be filtered.

Thus, Applicant realized that a filtering step retaining the dense fraction of the adipose tissue, namely the adipocytes, would avoid clogging problems during the subsequent separation step.

Furthermore, the method according to the present invention is particularly useful, because it allows separating regenerative cells from a heterogeneous cell population of a lipoaspirate adipose tissue liquid portion. Advantageously, the separated heterogeneous population of regenerative cells contains several different types of cells that are all useful in the body healing process. (Francis, Sachs et al., 2009)

Preferably, the first cut-off value is comprised between 45 microns and 60 microns and, more preferably comprised between 48 microns and 55 microns.

Preferably, the second cut-off value is comprised between 10 microns and 18 microns and, more preferably, comprised between 13 microns and 16 microns.

Preferably, step b) of separation of regenerative cellular components present in the liquid portion is performed by filtration or sedimentation techniques.

Preferably, step b) of separation of regenerative cellular components present in the liquid portion is performed by means of a microfluidic array.

Preferably, steps a)-c) of the method according to the present invention are carried out in a time ranging of from 1 to 5 minutes, depending on the amount of harvested adipose tissue, namely of harvested lipoaspirate.

Preferably, the recovered regenerative cellular components are stromal vascular fraction of the adipose tissue.

Preferably, the method according to the invention comprises a further step of separating regenerative cellular components present in the dense fraction.

More preferably, the separation of regenerative cellular component present in the dense fraction comprises:

Recovering a dense fraction of adipose tissue filtered from the liquid fraction in step a);

Adding saline solution to the recovered dense fraction of adipose tissue;

Subjecting the mixture of saline solution and dense fraction of adipose tissue to a homogenization step for reducing the dimension of adipocytes comprised within the dense fraction;

Centrifuging the homogenized mixture until phase separation and precipitation of the homogenized mixture takes place;

Recovering a pellet deriving from the phase separation and precipitation of the homogenized mixture.

Advantageously, in this way regenerative components from the dense fraction of the adipose tissue are extracted without the need of reagents to be added to the adipose tissue. This usefully allows extracting also the extracellular matrix of the regenerative cellular components without damaging it.

Preferably, the homogenization step for reducing the dimensions of adipocytes comprises subjecting the mixture of dense fraction of adipose tissue and saline solution to micronization.

Advantageously, in this way the adipocytes are reduced to a dimension in the range of microns.

More preferably, the micronization step comprises

Injecting a recovered first quantity of dense fraction of adipose tissue into a micronizer together with saline solution in the same first quantity;

Micronizing for a first preset time period;

Extracting the micronized mixture of dense fraction of adipose tissue and saline solution from the micronizer.

More preferably, the first preset time period is comprised between 30 seconds and 3 minutes, and more preferably is around 1 minute.

Preferably, the centrifuging step has a duration comprised between 3 minutes and 10 minutes, and more preferably equal to around 5 minutes.

Preferably, the recovered regenerative cellular components are stromal vascular fraction and extracellular matrix of the adipose tissue.

According to a second aspect of the present invention an assembly for extraction of regenerative cellular components from an adipose tissue is provided comprising a filtering element having a first cut-off value comprised between 40 microns and 70 microns for separating the liquid fraction from the dense fraction of a harvested adipose tissue; and a separation device having a second cut-off value ranging from 8 to 20 microns; and a recovering chamber for collecting the regenerative cells-rich fraction comprising the regenerative cellular components not having being blocked by the separation element.

Advantageously, the assembly for extraction of regenerative cellular components from an adipose tissue of the invention leads to the technical effects described above.

Preferably, the filtering element is comprised in a filtering pouch having a first inlet connector and a first outlet connector, the inlet and outlet connector being air-contamination free.

More preferably, the inlet connector and/or the outlet connector are needle free connectors.

More preferably, the filtering pouch comprises an air inlet provided with an air filter.

Preferably, the separation device comprises a closed chamber divided into two sub-chambers by a filtering mesh.

More preferably, the filtering mesh is anti-adhesion treated.

Even more preferably, the filtering mesh consists of a microfluidic array of lower than a value comprised between 8-20 microns, namely having filtering properties able to block particles with a size higher than 8-20 microns.

Advantageously, the anti-adhesion treatment is a treatment adapted to improve the pass-through capability of the filter, thereby minimizing clogging of the filter.

Preferably, the separation device comprises a second inlet connector and a second outlet connector, the second inlet and outlet connector being air-contamination free.

More preferably, the first outlet connector is connected to said second inlet connector by interposition of a one-way valve.

Preferably, the assembly for extraction of regenerative cellular components comprises a micronizing device and a centrifuging device.

Specific advantages of the method and assembly according to the present invention are the following:

it allows to collect a lipoaspirate adipose tissue without manipulation;

it allows to process a lipoaspirate adipose tissue in a sterile closed system;

it allows to obtain a regenerative cells fraction without any cell manipulation or reaction with any kind of drug or reagent;

it does not damage the cells directly and/or indirectly, being a manipulation-free process;

it requires a very short processing time, bringing therefore to a very low cellular damage.

BRIEF DESCRIPTION OF THE DRAWINGS

With reference to the attached drawings, further features and advantages of the present invention will be shown by means of the following detailed description of some of its preferred embodiments. According to the above description, the several features of each embodiment can be unrestrictedly and independently combined with each other in order to achieve the advantages specifically deriving from a certain combination of the same.

In the said drawings.

DETAILED DESCRIPTION OF CURRENTLY PREFERRED EMBODIMENTS OF THE INVENTION

Figure 1:
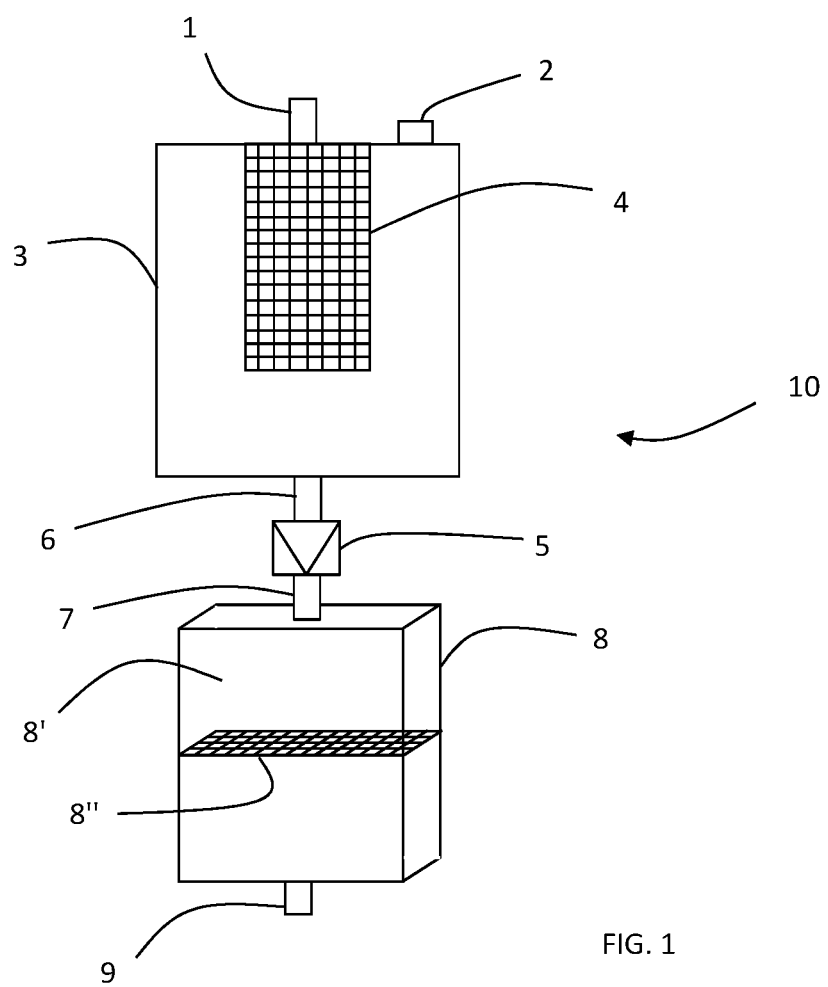
FIG. 1 is a schematic view of an assembly for extraction of regenerative cellular components from an adipose tissue in accordance with the present invention.
Figure 2:
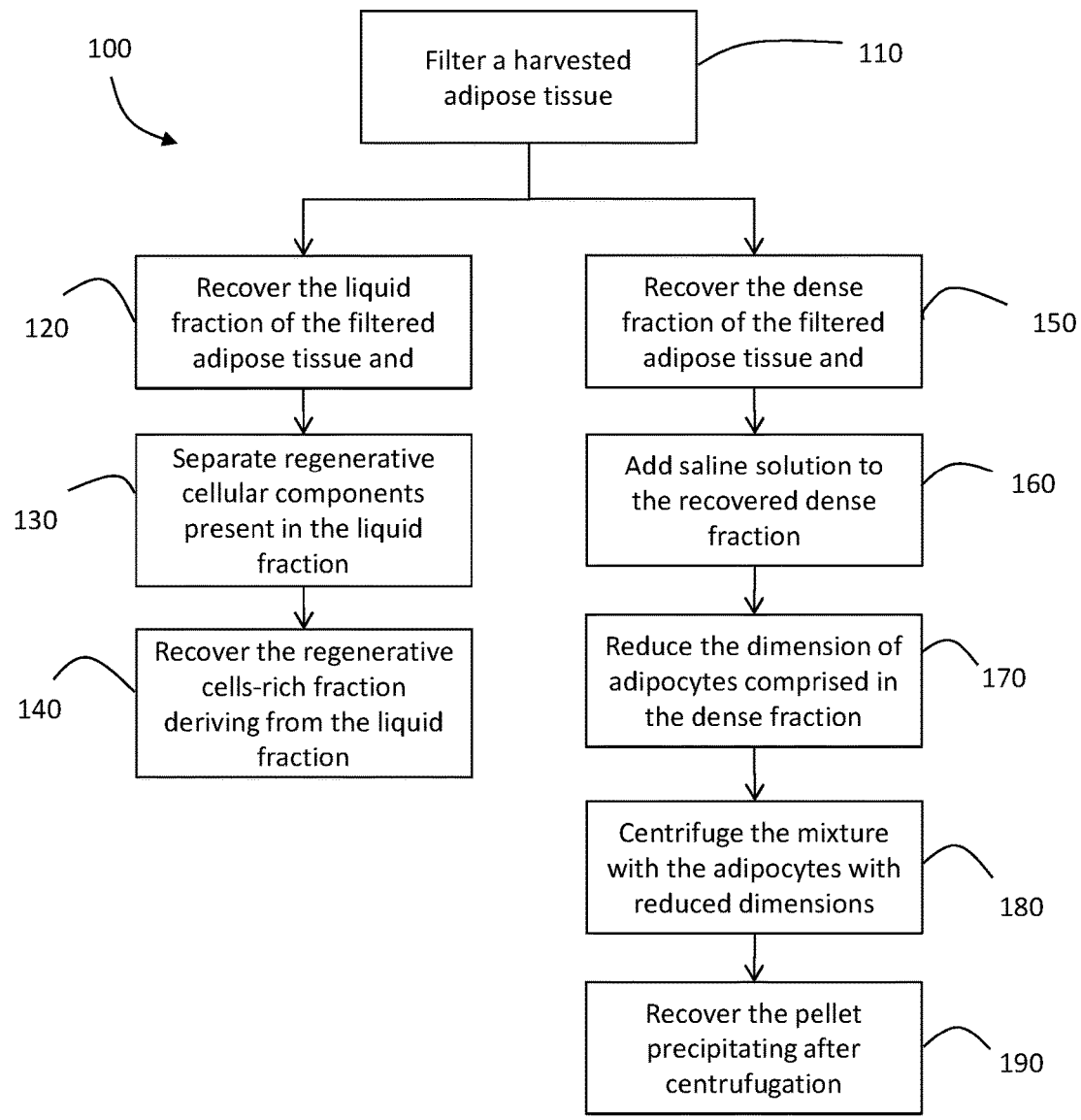
FIG. 2 is a flow chart of a method for extraction of regenerative cellular components from an adipose tissue according to an embodiment of the present invention.

In FIG. 1 the assembly for extraction of regenerative cellular components from an adipose tissue is globally indicated with 10.

The assembly 10 or extraction of regenerative cellular components from an adipose tissue comprises a medical grade plastic filtering pouch 3,4 for the separation of the adipose tissue from its liquid component and a separation device 8 for separating unwanted cellular components from the regenerative cellular components.

Both, the filtering pouch 3 and the separation device 8 have an inlet connector 1,7 and an outlet connector 6,9. The inlet connector 1 of the filtering pouch 3 allows feeding the adipose tissue into the filtering pouch 3. The outlet connector 6 of the filtering pouch allows collecting the filtered liquid fraction of the adipose tissue. The inlet connector 7 of the separation device 8 allows feeding the liquid fraction of the adipose tissue into the separation device 8. The outlet connector 9 of the separation device 8 allows collecting the separated regenerative cellular components deriving from the liquid fraction of the adipose tissue.

The filtering pouch 3 comprises also an air inlet with an air filter 2.

Inside the filtering pouch 3 a filtering element 4 is provided.

Preferably, the filtering element 4 is a medical grade bag provided with micron filtering walls. The micron filtering walls are adapted to block particles having a size greater than a first cut-off value preferably comprised between 40 microns and 70 microns, more preferably comprised between 45 microns and 60 microns and, even more preferably comprised between 48 microns and 55 microns. In this way, adipocytes and other unwanted elements are blocked by the micron filtering bag 4, whereas the liquid fraction of the adipose tissue passes through. Preferably, the medical grade bag 4 is rectangular.

In the embodiment of FIG. 1, the outlet 6 of filtering pouch 3 and the inlet 7 of the separation device 8 are connected one to another by means of a one-way valve 5 for allowing only the liquid flow from the filtering pouch 3 to the separation device 8.

However, in further preferred embodiments (not shown) the filtering pouch 3 and the separation device 8 are separated one from the other and the transfer of the liquid fraction from the filtering pouch 3 to the separation device 8 takes place by means of syringes, preferably of the luer lock type.

According to the embodiment of FIG. 1, the filtering pouch 3 is placed above the separation device 8 so that the liquid fraction of the adipose tissue flows from the filtering pouch 3 to the separation device 8 by gravity.

In this way, the separation device 8 receives a continuous flow of fluid, namely the liquid fraction of the adipose tissue, from the filtering pouch 3 placed above the same 8 in a closed and sterile way, without any manipulation.

In the embodiment shown in FIG. 1, the separation device 8 comprises a closed collecting chamber 8' where a filtering anti-adhesion mesh 8" receives the fluid flow from the filtering pouch 3 placed above, through the one-way valve 5. The closed chamber 8' is preferably rectangular and made of plastic material, e.g. PVC.

The separation device 8 retains in its collecting chamber 8' part of the unwanted cells present in the liquid fraction of the adipose tissue, namely cells having a size above a second cut-off value preferably comprised between 8 and 20 micron, more preferably comprised between 10 microns and 18 microns and, even more preferably, comprised between 13 microns and 16 microns.

Only the regenerative cells of a size preferably smaller than the second cut-off value flush through the separation device 8 for being collected in a recovering chamber (not shown), e.g. a syringe.

In order to obtain a closed sterile system, needle free connectors are used as inlet 1,7 and outlet 6,9 connectors. Needle free connectors allow access to the filtering pouch 3 and/or the separation device 8 only when a luer lock syringe tip is pressed and twisted on the same, thereby avoiding air contamination.

The assembly 10 according to the invention advantageously also comprises a micronizing device (not shown) and a centrifuging device (not shown) for recovering regenerative cellular components from the dense fraction collected into the filtering element 4 of the filtering pouch 3.

In an embodiment of the method 100 according to the present invention, after harvesting a small amount of adipose tissue using e.g. a syringe lipoplasty technique, the adipose syringe (not shown) is connected to the inlet connector 1 of the filtering pouch 3 and its content is injected inside the filtering pouch 3.

The harvested adipose tissue reaches the filtering bag 4 inside the filtering pouch 3 where it is filtered (step 110) so that particles greater than the first cut-off value are blocked, namely the adypocites, and the liquid fraction flows through (step 120). In this way, the dense fraction of the adipose tissue is collected in the filtering bag 4.

Subsequently, the liquid fraction is processed (steps 130, 140) to recover the regenerative cellular components contained in the same.

The processing is preferably carried out through a filtering anti-adhesion mesh 8", which is a microfluidic array performing the separation process through a size segregation technique.

Alternatively, also a sedimentation technique can be applied for the separation of the regenerative cellular components from the other components contained in the liquid fraction of the adipose tissue.

The liquid fraction rich in regenerative components flows into the microfluidic array 8", where only unwanted cells, namely cells having a size bigger than the second cut-off value, are blocked. (step 130).

The liquid flow in the assembly 10 according to the present invention starts when a vacuum recovering chamber (not shown), e.g. a vacuum syringe is connected to the outlet connector 9 of the separation device 8. The recovering chamber collects the regenerative cell liquid suspension that flows through the microfluidic array 8".

All the regenerative cellular components having a size smaller than the second cut-off value are so collected in the recovering chamber. (step 140)

The method also comprises a step of separating regenerative cellular components present in the dense fraction (step 150). To perform this separation the dense fraction of adipose tissue filtered from the liquid fraction is collected from the filtering bag 4.

The collected dense fraction is injected into a micronizer together with saline solution (step 160) in equal quantities, in order to subject the mixture of saline solution and dense fraction of adipose tissue to micronization, namely a homogenization step for reducing the dimension of adipocytes comprised within the dense fraction. (step 170)

The homogenized mixture is then extracted from the micronizer and subjected to centrifugation (step 180) until phase separation and precipitation of the homogenized mixture takes place. In detail, the output of the centrifuging step is a three-phase liquid comprising an oil phase at the surface, a fluid phase in the middle and a lower solid phase, called pellet. The pellet contains the regenerative cellular components of the dense fraction of the adipose tissue, namely Stromal Vascular Fraction (SVF) and extracellular matrix (ECM). Thus, the pellet is finally recovered (step 190) e.g. by means of an appropriate syringe (not shown).

Preferably, the micronization has a duration comprised between 30 seconds and 3 minutes and, and more preferably is around 1 minute.

Preferably, the centrifuging step has a duration comprised between 3 minutes and 10 minutes, and more preferably equal to around 5 minutes.

All the method steps are preferably performed at room temperature.

The invention claimed is:

1. A method for extracting regenerative cellular components from adipose tissue comprising the steps of:
   a) filtering a harvested adipose tissue for recovering its liquid fraction by means of a filtering element having a first cut-off value between 40 microns and 70 microns;
   b) separating regenerative cellular components present in the liquid fraction by means of cell size segregation, which blocks cells bigger than a second cut-off value ranging from 8 to 20 microns; and
   c) recovering the liquid regenerative cells-rich fraction comprising the regenerative cellular components not having being blocked during the separating step b);
   wherein steps a)-c) are carried out in a time ranging from 1 to 5 minutes.

2. The method according to claim 1, wherein the first cut-off value is between 45 microns and 60 microns.

3. The method according to claim 1, wherein the second cut-off value is between 10 microns and 18 microns.

4. The method according to claim 1, wherein step b) of separation of regenerative cellular components present in the liquid fraction is performed by filtration or sedimentation techniques or by means of a microfluidic array.

5. The method according to claim 1, wherein the recovered regenerative cellular components are a stromal vascular fraction of the adipose tissue.

6. A method for extracting regenerative cellular components from adipose tissue comprising the steps of:
   a) filtering a harvested adipose tissue for recovering its liquid fraction by means of a filtering element having a first cut-off value between 40 microns and 70 microns;
   b) separating regenerative cellular components present in the liquid fraction by means of cell size segregation, which blocks cells bigger than a second cut-off value ranging from 8 to 20 microns;
   c) recovering the liquid regenerative cells-rich fraction comprising the regenerative cellular components not having being blocked during the separating step b); and
   d) separating regenerative cellular components present in a dense fraction filtered from the liquid fraction in step a).

7. The method according to claim 6, wherein the separation of regenerative cellular component present in the dense fraction of step d) comprises:
   recovering a dense fraction of adipose tissue filtered from the liquid fraction in step a);
   adding saline solution to the recovered dense fraction of adipose tissue;
   subjecting the mixture of saline solution and dense fraction of adipose tissue to a homogenization step for reducing the dimension of adipocytes comprised in the dense fraction;
   centrifuging the homogenized mixture until phase separation and precipitation of the homogenized mixture takes place; and
   after centrifugation recovering a pellet deriving from the phase separation and precipitation of the homogenized mixture.

8. The method according to claim 7, wherein the homogenization step for reducing the dimensions of adipocytes comprises subjecting the mixture of the dense fraction of adipose tissue and saline solution to micronization.

9. The method according to claim 8, wherein the micronization step comprises:
   injecting a recovered first quantity of the dense fraction of adipose tissue into a micronizer together with saline solution in the same first quantity;
   micronizing for a first preset time period;
   extracting the micronized mixture of the dense fraction of adipose tissue and saline solution from the micronizer.

10. The method according to claim 9, wherein the first preset time period is between 3 minutes and 30 seconds.

11. The method according to claim 9, wherein the centrifuging step has a duration between 10 minutes and 3 minutes.

12. A method for extracting regenerative cellular components from adipose tissue comprising the steps of:
   a) filtering a harvested adipose tissue for recovering its liquid fraction by means of a filtering element having a first cut-off value between 40 microns and 70 microns;
   b) separating regenerative cellular components present in the liquid fraction by means of cell size segregation, which blocks cells bigger than a second cut-off value ranging from 8 to 20 microns; and
   c) recovering the liquid regenerative cells-rich fraction comprising the regenerative cellular components not having being blocked during the separating step b);
   wherein steps a)-c) are carried out at room temperature.

13. An apparatus for extraction of regenerative cellular components from an adipose tissue comprising:
   a filtering element in a filtering pouch having a first inlet connector and a first outlet connector, the first inlet and first outlet connectors being air-contamination free, the filtering element having a first cut-off value between 40 microns and 70 microns for separating the liquid fraction from the dense fraction of a harvested adipose tissue;
   a separation device having a second cut-off value ranging from 8 to 20 microns; and a recovering chamber for collecting the regenerative cells-rich fraction comprising the regenerative cellular components not having being blocked by the separation device.

14. The apparatus according to claim 13, wherein the first inlet connector and/or the first outlet connector are needle free connectors.

15. The apparatus according to claim 13, wherein the filtering pouch comprises an air inlet with an air filter.

16. The apparatus according to claim 13, wherein the separation device comprises a second inlet connector and a second outlet connector, the second inlet and second outlet connectors being air-contamination free.

17. The apparatus according to claim 16, wherein the first outlet connector of the filtering pouch in the filtering element is connected to said second inlet connector of the separation device by interposition of an one-way valve.

18. The apparatus according to claim 13 further comprising a micronizing device and a centrifuging device.

19. The method according to claim 2, wherein the first cut-off value is between 48 microns and 55 microns.

20. The method according to claim 3, wherein the second cut-off value is between 13 microns and 16 microns.

21. The method according to claim 10, wherein the first preset time period is about 1 minute.

22. The method according to claim 11, wherein the centrifuging step has a duration equal to about 5 minutes.

23. The method according to claim 6, wherein the second cut-off value is between 10 microns and 18 microns.

24. The method according to claim 6, wherein step b) of separation of regenerative cellular components present in the liquid fraction is performed by filtration or sedimentation techniques or by means of a microfluidic array.

25. The method according to claim 6, wherein the recovered regenerative cellular components are a stromal vascular fraction of the adipose tissue.

26. The method according to claim 12, wherein the second cut-off value is between 10 microns and 18 microns.

27. The method according to claim 12, wherein step b) of separation of regenerative cellular components present in the liquid fraction is performed by filtration or sedimentation techniques or by means of a microfluidic array.

28. The method according to claim 12, wherein the recovered regenerative cellular components are a stromal vascular fraction of the adipose tissue.

* * * * *